(12) United States Patent
Lenting et al.

(10) Patent No.: US 6,973,689 B2
(45) Date of Patent: Dec. 13, 2005

(54) DOCKING MEANS FOR MEDICAL SYSTEM COMPRISING EXAMINATION DEVICE AND PATIENT SUPPORT DEVICE

(75) Inventors: Gerrit Jan Lenting, Eindhoven (NL); Wilhelmina Margareta Joseph Mertens, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/495,525

(22) PCT Filed: Oct. 25, 2002

(86) PCT No.: PCT/IB02/04509

§ 371 (c)(1),
(2), (4) Date: Oct. 1, 2004

(87) PCT Pub. No.: WO03/041577

PCT Pub. Date: May 22, 2003

(65) Prior Publication Data

US 2005/0034237 A1    Feb. 17, 2005

(30) Foreign Application Priority Data

Nov. 14, 2001   (EP) ................................. 01204347

(51) Int. Cl.[7] .............................................. A61B 6/04
(52) U.S. Cl. ........................ 5/601; 378/209; 600/415
(58) Field of Search ....................... 5/601; 378/209; 600/415

(56) References Cited

U.S. PATENT DOCUMENTS

| 4,567,894 | A | * | 2/1986 | Bergman | 600/415 |
|---|---|---|---|---|---|
| 4,727,328 | A | * | 2/1988 | Carper et al. | 324/318 |
| 5,199,123 | A | * | 4/1993 | Jacques et al. | 5/601 |
| 5,499,415 | A | * | 3/1996 | McKenna | 5/601 |
| 5,525,905 | A | * | 6/1996 | Mohapatra et al. | 324/318 |
| 6,459,923 | B1 | * | 10/2002 | Plewes et al. | 600/411 |
| 6,640,364 | B1 | * | 11/2003 | Josephson et al. | 5/601 |
| 6,776,527 | B1 | * | 8/2004 | Tybinkowski et al. | 378/209 |

FOREIGN PATENT DOCUMENTS

| JP | 9299352 | 11/1997 |
|---|---|---|
| JP | 11033010 | 2/1999 |

* cited by examiner

Primary Examiner—Michael Trettel
(74) Attorney, Agent, or Firm—Thomas M. Lundin

(57) ABSTRACT

A medical system for examination of a patient, comprising an examination device (1), a patient support device (13,15), and docking means for connecting both said devices to each other. The docking means comprises a first part (21) provided with a guiding member (57) and a second part (19) provided with guiding elements (61,63) for contacting the guiding surface (59). Each of said parts (19,21) is attached to one of said devices. The guiding member (57) comprises two substantially vertical guiding surfaces (59), positioned symmetrically with respect to a vertical plane through the device (1) to which the first part (21) of the docking means is attached. The distance between said two guiding surfaces (59) decreases further away from the device (1) to which said first part (21) is attached.

13 Claims, 4 Drawing Sheets

Figure 1:
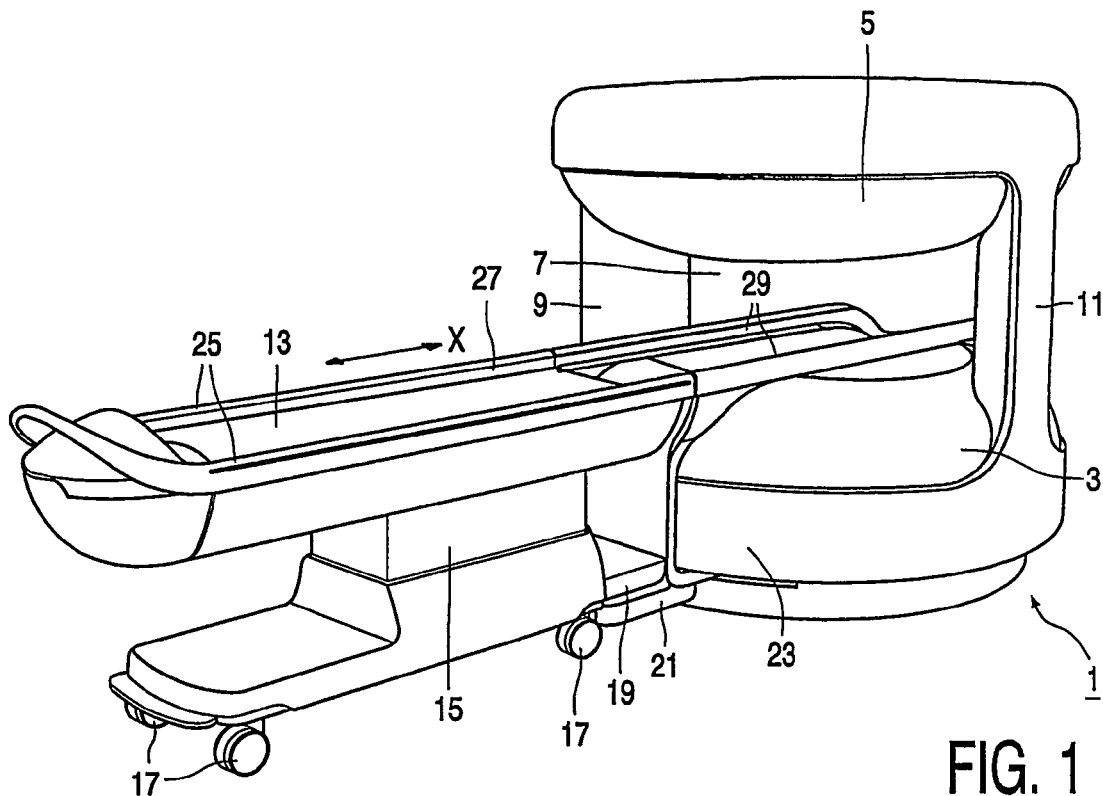

DOCKING MEANS FOR MEDICAL SYSTEM COMPRISING EXAMINATION DEVICE AND PATIENT SUPPORT DEVICE

The invention is related to a medical system for examination or treatment of a patient, comprising an examination device, a patient support device, and docking means for connecting both said devices to each other, the docking means comprising a first part provided with a guiding member having a guiding surface and a second part provided with guiding elements for contacting the guiding surface, whereby each of said parts is attached to one of said devices.

Although the medical system according to the invention can be an examination system as well as a treatment system, the system will be referred to as examination system. In consequence, the medical examination system and the examination device as described in the specification and in the claims also include a medical treatment system and a treatment device respectively.

The system may be a medical imaging system, whereby images can be made of the entrails of the body of a patient by making use of magnetic resonance imaging methods. The examination device of such system comprises an electrical coil system for generating a varying magnetic field and radio-frequency signals in an examination volume, in which the patient is to be placed. The electrical coil system also receives radio-frequency signals generated by the body of the patient in response to the radio-frequency signals generated by the coil system.

The patient support device can be a trolley provided with a horizontal bed, i.e. a support unit on which the patient can lie. By making use of the docking means, the trolley can be connected to the examination device, after which the bed—with the patient lying on it—can be displaced from the trolley into said examination volume of the examination device, so that the patient can be subjected to an examination. After examination of the body of the patient the bed with the patient is displaced to the trolley again, so that the patient support device can be disconnected from the examination device and can be moved away. By making use of more then one patient support device, the examination device can be used intensively.

Before the patient support device can be connected to the examination device, the patient support device must be positioned at an exact location and in an exact position with respect to the examination device. That location and position is difficult to find by the human operator of the patient support device. However, it is not recommended to move the patient support device to the exact target location and position by means of automatic motions and the like, because of safety reasons. The operator should always remain in control of the movement of the patient support device.

An object of the invention is to provide docking means for connecting a patient support device to a medical examination device, whereby an effective and efficient docking operation can take place.

In order to accomplish that objective, the guiding member comprises two substantially vertical guiding surfaces, positioned symmetrically with respect to a vertical plane through the device to which the first part of the docking means is attached, whereby the distance between said two guiding surfaces decreases further away from the device to which said first part is attached. Such two guiding surfaces push the second part of the docking means in the correct position when the guiding elements are moving against it towards the device to which said first part of the docking means is attached.

Preferably, said first part of the docking means is attached to the medical examination device, and said second part is attached to the patient support device. Especially in case more then one patient support device is used in combination with one medical examination device it is advantageously to have the more complex part of the docking means attached to the medical examination device.

In one preferred embodiment said guiding member is movable with respect to the said first part. Thereby the guiding member can positively guide the movement of the patient support device before it reaches its final position. Especially in case the patient support device is riding over the floor by hinging rollers, an additional movement of the device facilitates exact positioning of the device.

Preferably, said guiding member is movable in one horizontal direction towards and away from the device to which said first part is attached, whereby means for pushing the guiding member in a position away from that device may be present. After said second part of the docking means contacts the guiding member, the patient support device can be positioned relative to the guiding member during its movement in said horizontal direction.

In one preferred embodiment said guiding member is a substantial horizontal plate-like element, whereby the edge of said plate-like element forms said guiding surface. Said plate-like element may form the upper wall of the first part of the docking means.

Preferably, said docking means are located at the lower parts of said devices, i.e. near the floor on which the examination device is placed and on which the patient support device is moved. Such low location of the docking means increases the stability of the devices during and after the docking operation.

Preferably, said guiding element for contacting the guiding surface comprises a roller that can roll over said guiding surface, ensuring a smooth movement of said second part of the docking means relative to the guiding member.

In one preferred embodiment said first part of the docking means comprises damping means for braking down the movement of the guide member when it reaches its final position whereby the two parts of the docking means are interconnected. Thereby said damping means may comprise a pneumatic cylinder counter-acting the movement of the guiding member, especially the last portion of the movement towards the device to which said first part is attached. Such damping action increases comfort for the patient as well as for the operator of the docking action, and avoids damage of the system.

Preferably, coupling means are present for fixing said first part to said second part of the docking means after the two parts are moved towards each other. Said coupling means may comprise two protrusions of said second part and two corresponding recesses in said first part, the recesses being located at both substantial vertical opposite sides of said first part, whereby preferably said recesses and portions of said first part near said recesses can move towards each other.

In one preferred embodiment the docking means comprise a connector for power and/or signals, which connector comprises a first portion in said first part and a second portion in said second part of the docking means, whereby said portions are movable towards each other for mutual engagement after both said devices are connected to each other. At that moment the two portions are positioned in an exact predetermined mutual position, so that a simple linear movement of one of the portions will result in said mutual engagement. Such docking of the two portions of the connector can take place automatically by an actuator after the docking operation of the two parts of the docking means has terminated.

Figure 2:
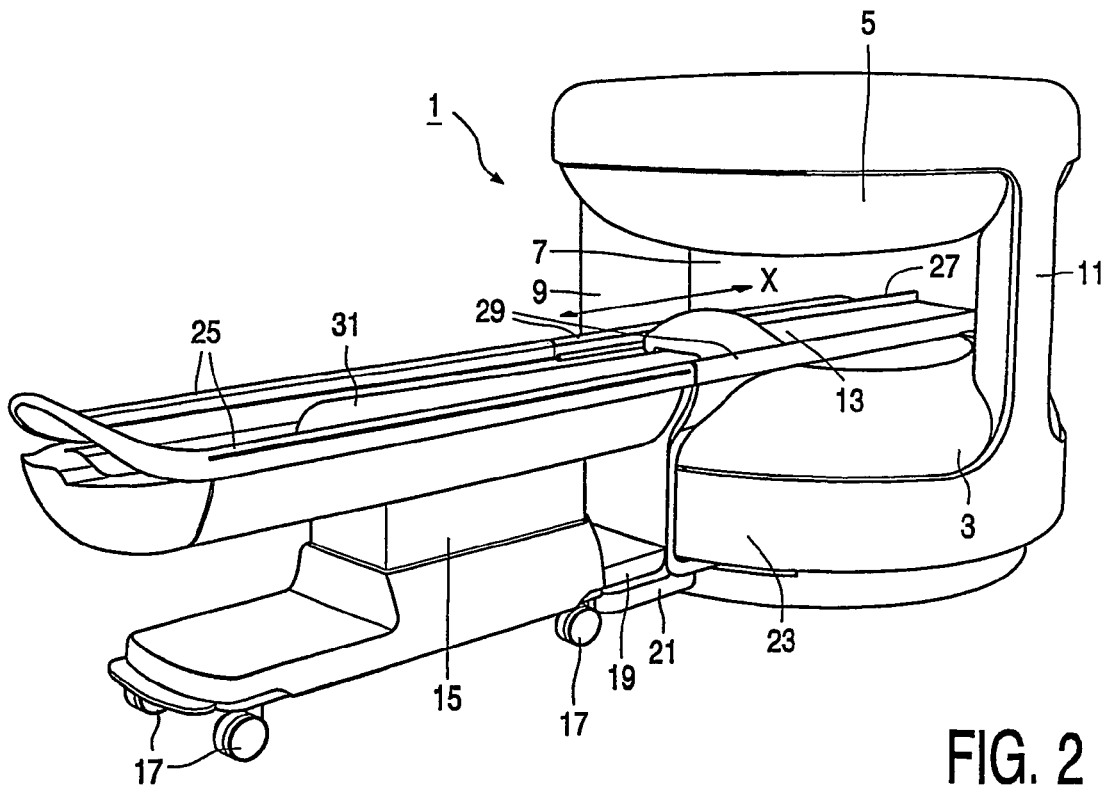
Figure 3:
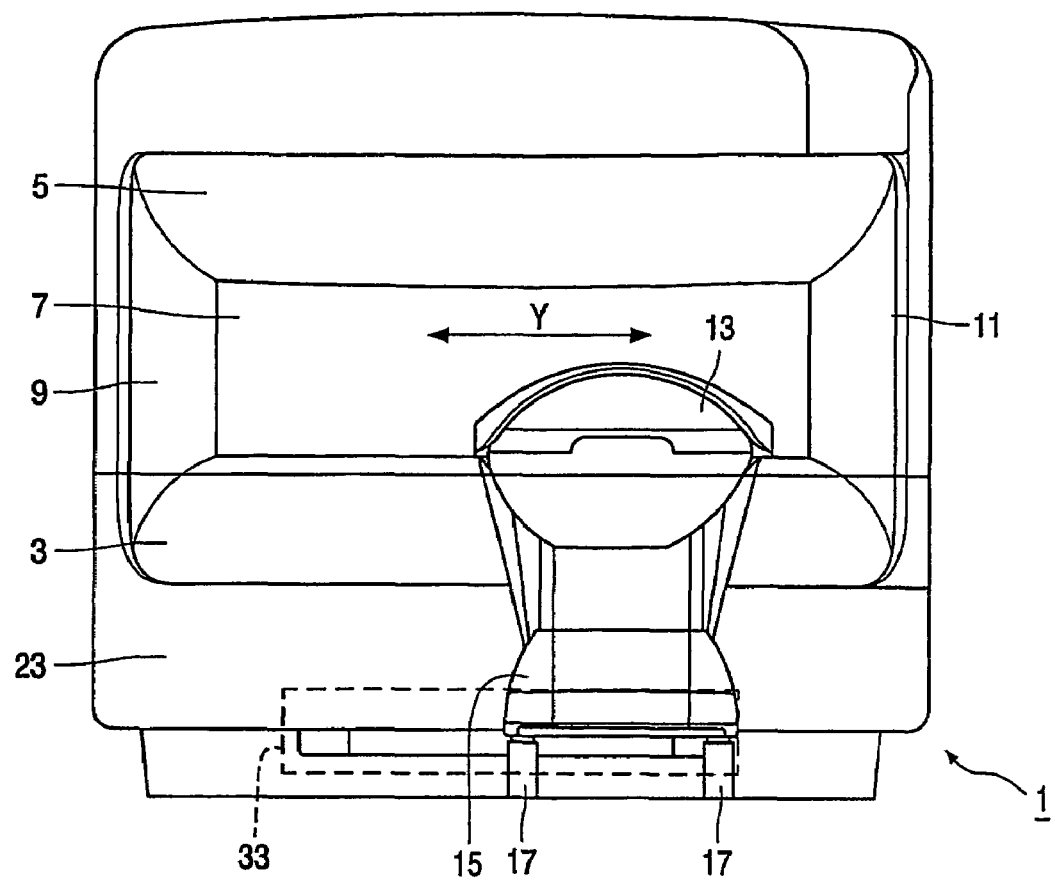
Figure 4:
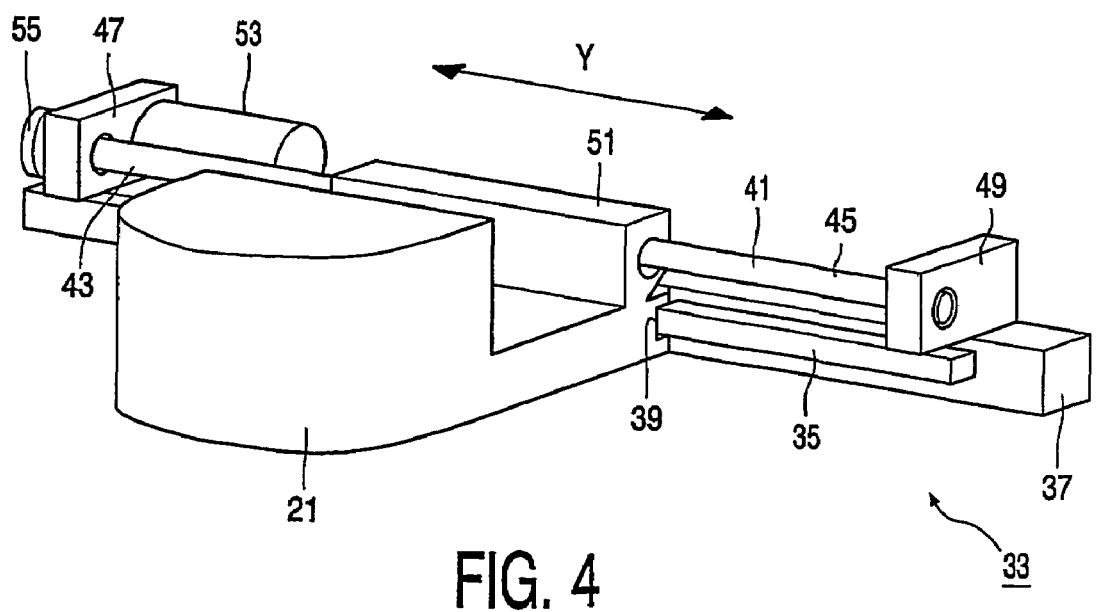
Figure 5:
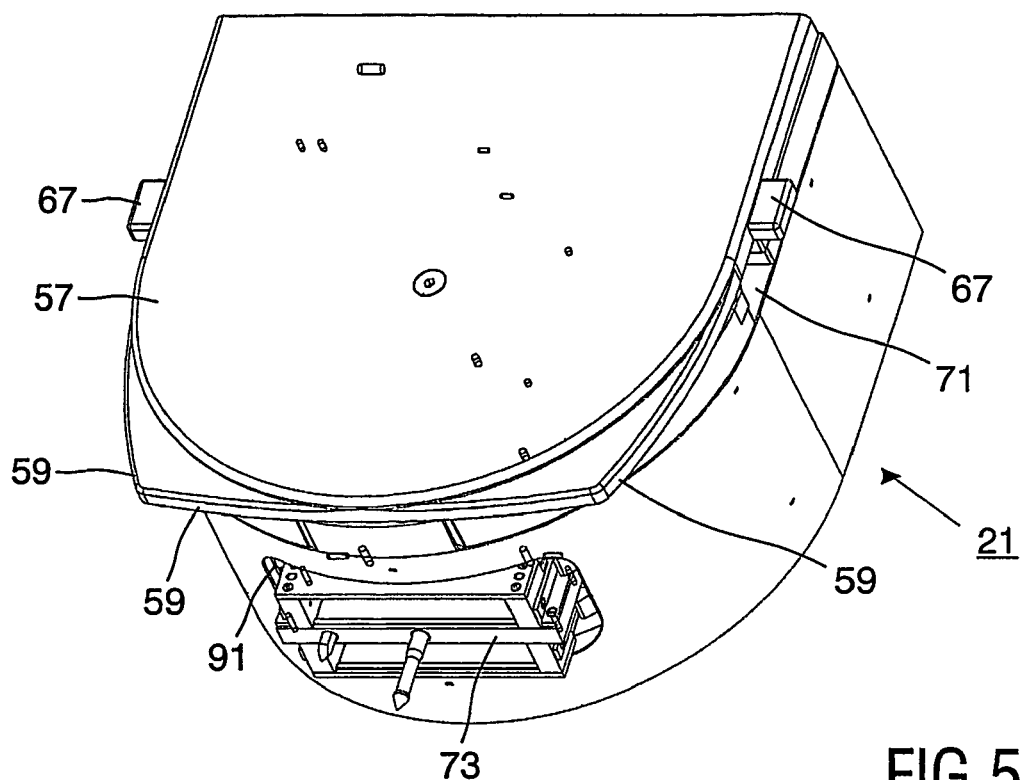
Figure 6:
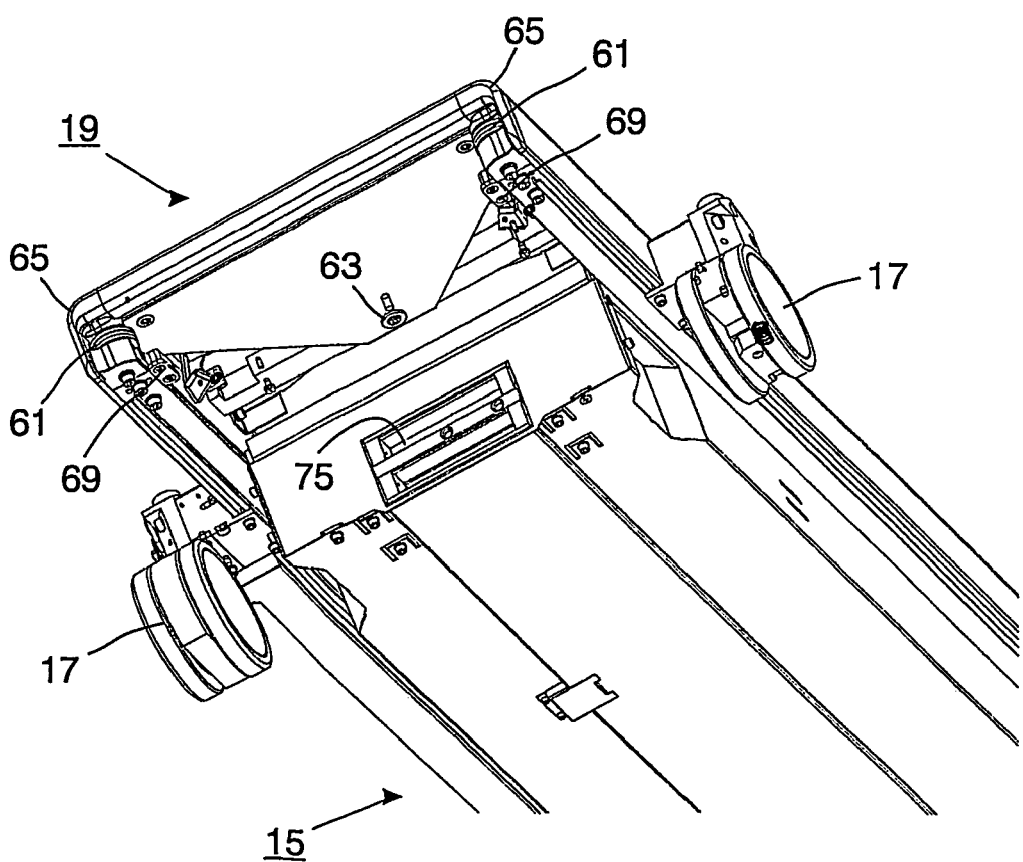
Figure 7:
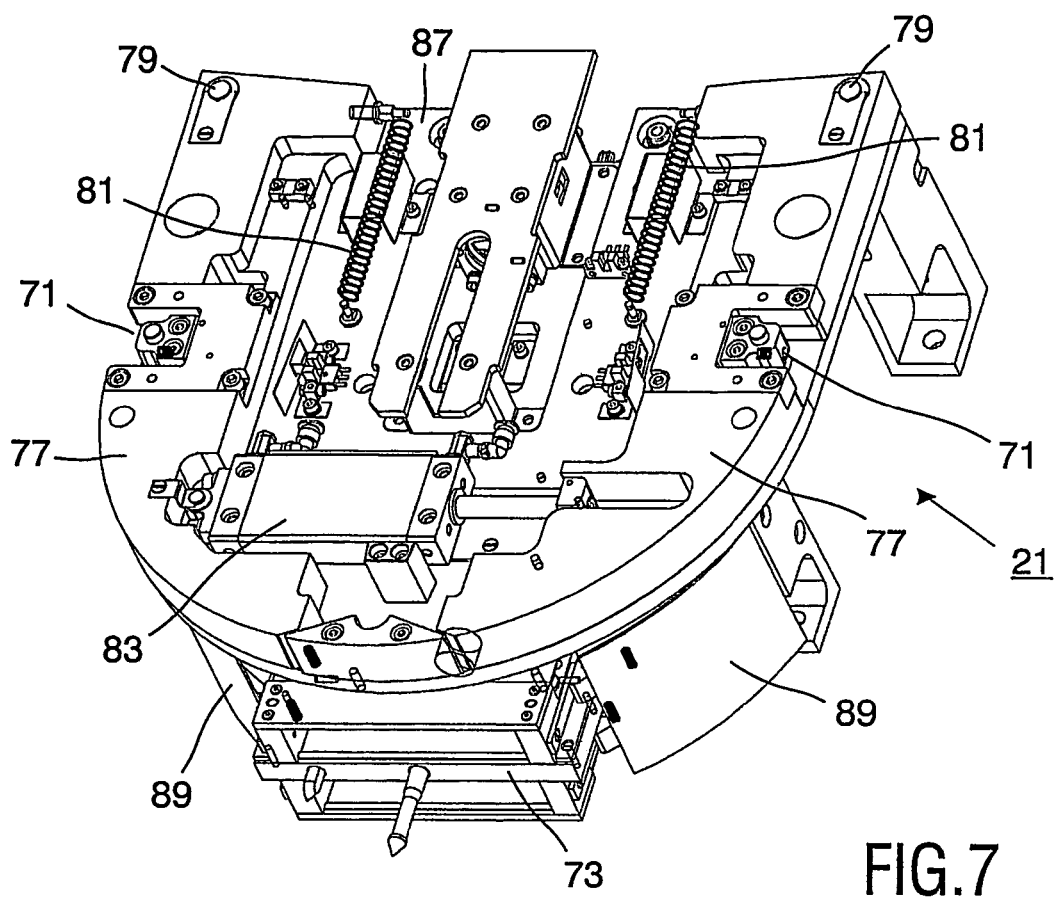
Figure 8:
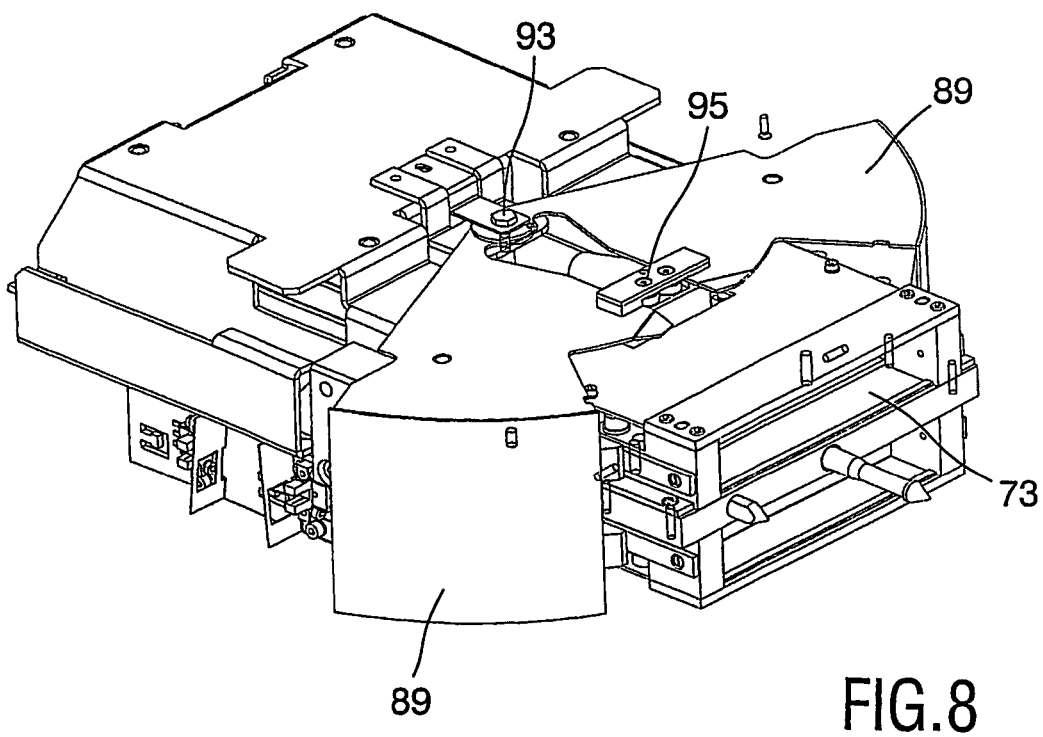

The invention will be explained in more detail hereinafter by means of a description of an embodiment of a medical system, in which reference is made to a drawing, in which:

FIG. 1 shows a medical examination system,
FIG. 2 shows the system in another position,
FIG. 3 is a front view of the medical examination system,
FIG. 4 shows the first part of the docking means,
FIG. 5 shows the first part of the docking means in more detail,
FIG. 6 shows the second part of the docking means,
FIG. 7 shows the first part of the docking means without the guiding member, and
FIG. 8 shows a portion of the first part of the docking means.

The figures are merely schematic representations of the embodiment, in which less relevant parts are not shown.

The medical examination system shown in FIGS. 1, 2 and 3 is a magnetic resonance imaging system of the so-called open type. The system can make images of the entrails of a patient by using a magnetic resonance imaging method. The medical examination system comprises an examination device 1 having a lower coil system housing 3 and an upper coil system housing 5, which accommodate an electrical coil system. The coil system itself is not shown in the figures, and it can be of a kind that is known per se. Between the lower coil system housing 3 and the upper coil system housing 5, an examination volume 7 is present, in which the patient is to be placed. Two vertical columns 9,11 of the examination device 1 interconnect the lower coil system housing 3 and the upper coil system housing 5.

During operation of the medical examination system, the coil system generates a varying magnetic field and radio-frequency signals in the examination volume 7. In response to the radio-frequency signals generated by the coil system, the patient's body generates radio-frequency signals, which are received by the coil system and are processed into an image of the patient's body.

The medical examination system further comprises a patient support device consisting of a horizontal bed 13 and a mobile carrier 15, carrying the horizontal bed 13. The mobile carrier 15 is a trolley that is mobile by means of rolling members 17 and that can be connected to the examination device 1 by docking means 19,21. A first part 21 of the docking means is attached to the examination device 1, in particular at the front side 23 of the lower coil system housing 3. A second part 19 of the docking means is attached to the mobile carrier 15. The docking means 19,21 are only schematically shown in FIGS. 1 and 2.

By making use of the docking means 19,21 the mobile carrier 15 of the patient support device can be mechanically coupled to and uncoupled from the lower coil system housing 3, so that the horizontal bed 13 can be brought in a pre-defined stable position relative to the examination device 1.

Since the patient support device 13,15 is mobile, it can be moved with the patient lying on it. Thereby it can transport the patient from the medical examination device 1 to, for example, a separate preparation room, where the patient was prepared before the examination, or to another medical examination or treatment device to undergo a subsequent examination or treatment. Preferably the medical system comprises at least two patient support devices 13,15. In this manner, a next patient can be prepared during the examination or treatment of the preceding patient. As a result, the medical system can be efficiently used.

In the docked position of the mobile carrier 15 shown in FIG. 1, the horizontal bed 13—with the patient lying on it—can be displaced relative to the mobile carrier 15 and relative to the examination device 1 in a first horizontal direction X. Thereby the bed can be moved from a first position shown in FIG. 1 to a second position shown in FIG. 2. In said first position the bed 13 is fully supported by the mobile carrier 15 and in said second position the bed 13 is present in the examination volume 7 of the examination device 1. For that purpose, the mobile carrier 15 is provided with a first guide member 25 which, in the docked condition of the mobile carrier 15, extends in the first horizontal direction X and co-operates with guide elements 27 provided on the bed 13. The examination device 1 is provided with a second guide member 29, which is present in the examination volume 7 and extends in the first horizontal direction X and which, in the docked condition of the mobile carrier 15, is in line with said first guide member 25.

The mobile carrier 15 further comprises a first displacement device for displacing the horizontal bed 13 along said first guide member 25 and along said second guide member 29 into the examination volume 7 and, after the examination of the patient, out of the examination volume 7 again. Said first displacement device may be of a conventional kind and may be provided, for example, with an elongate push-pull member 31, shown in FIG. 2, which is fastened to the bed 13 and is driven by an electrical motor provided in the mobile carrier 15. When the horizontal bed 13 is displaced by said first displacement device into the examination volume 7, the guiding and supporting functions of said first guide member 25 of the mobile carrier 15 are taken over by said second guide member 29. When the bed 13 is displaced out of the examination volume 7, the guiding and supporting functions of said second guide member 29 are taken over again by said first guide member 25.

As shown in FIG. 3, the medical examination system further comprises a second displacement device 33 by means of which the horizontal bed 13, in the docked condition of the mobile carrier 15, can be displaced relative to the examination device 1 in a second horizontal direction Y transverse to the first horizontal direction X. The portion of the patient's body to be examined can be brought in a correct position relative to the examination device 1 by displacing the patient relative to the examination device 1 in said second horizontal direction Y.

In order to allow the horizontal bed 13 to be displaced in the second horizontal direction Y relative to examination device 1 in a stable manner, said second displacement device 33 is provided on the lower coil housing 3 of the examination device 1. Thereby the first part 21 of the docking means is moved relative to examination device 1 in said second horizontal direction Y. FIG. 3 only schematically shows said second displacement device 33 by means of broken lines. FIG. 4 schematically shows the main parts of said second displacement device 33.

Said second displacement device 33 comprises a linear guide member 35, which extends in the second horizontal direction Y. Linear guide member 35 is mounted to a frame member 37 which is attached to the lower coil system housing 3. The first part 21 of the docking means, which is only schematically shown in FIG. 4, comprises a guide element 39 for co-operating with said linear guide member 35.

The second displacement device 33 further comprises a spindle 41, which also extends in said second horizontal direction Y and which is provided with a screw-thread not shown in FIG. 4. A first end portion 43 and a second end portion 45 of the spindle 41 are journalled respectively in a first bearing bush 47 and in a second bearing bush 49, both bushes are mounted to the frame 37. A third bearing bush 51, which comprises an internal screw thread for co-operating with the screw thread of the spindle 41, is mounted to said first part 21 of the docking means. The second displacement device 33 further comprises an electrical motor 53 mounted to the frame member 37 for driving a gear wheel 55 which is mounted to the first end portion 43 of the spindle 41. When the gear wheel 55 is driven by the motor 53, the first part 21 of the docking means 21 is displaced along the linear guide member 35 as a result of the co-operation between the screw-thread spindle 41 an of the third bearing bush 51.

With the above constitution of the second displacement device 33, movements of the horizontal bed 13 relative to the examination device 1 in the second direction Y are generated in the docked condition of the mobile carrier 15 by displacing the first part 21 of the docking means, together with the mobile carrier 15 and the horizontal bed 13. Thereby the rolling members 17 provide a stable support of the mobile carrier 15 during its displacement in the second horizontal Y direction.

The horizontal movement in Y direction of the first part 21 of the docking means is an option. In other embodiments of the invention, the first part 21 of the docking means is attached to the lower coil system housing 3 at a fixed location, so that it can not move in horizontal direction.

FIG. 5 is a perspective view of the first part 21 of the docking means, which part is attached to the examination device 1, and FIG. 6 is a perspective view of a portion of the mobile carrier 15, showing the second part 19 of the docking means. Both parts 19,21 and their cooperation will be described hereinafter.

FIG. 5 shows the upper side of said first part 21, which upper side is provided with a plate-like guiding member 57. The outer edge 59 of the plate-like guiding member 57 forms a substantial vertical guiding surface for contacting the guiding elements 61,63 (see FIG. 6).

FIG. 6 shows the lower side of a portion of the mobile carrier 15, including two of the four roller members 17. Near both corners at the front side of the second part 19 of the docking means there are two guiding elements 61, and at a distance of that front side there is provided a third guiding element 63. Each of the three guiding elements 61,63 is a roller, which can revolve around a vertical axis.

When the patient support device 13,15 is moved to the examination device 1, the guiding elements 61,63 will contact the guiding surface 59 of the guiding member 57, i.e. de rollers 61,63 will contact the outer edge 59 of the plate-like guiding member 57. When one guiding element 61 contacts the guiding surface 59, the further movement of the mobile carrier 15 will be guided by that guiding element 61 while it rolls over the guiding surface 59. The further movement will result in a mutual position of the two parts 19,21 of the docking means, whereby all three rollers 61,63 are in contact with the edge 59 of the guiding member 57. Thereby the two corner portions 65 of the second part 19 of the docking means will contact the stops 67 at the edge 59 of the guiding member 57, so that the guiding member 57 will be moved backwards guiding the mobile carrier 15 to its final docked position. In that final position two protrusions 69 of the second part 19 of the docking means will engage with two recesses 71 in the first part 21 of the docking means, resulting in a mutual fixation of both parts 19,21 of the docking means.

In case one of the two corner portions 65 contacts a stop 67, then the patient support device 13,15 will automatically reaches its correct final position after the operator pushes the patient support device further towards the examination device 1, whereby the other corner portion 65 will contact the other stop 67.

The last part of the movement of the patient support device 13,15 towards the examination device 1 is damped by damping means that reduce the speed of the movement of the guiding member 57. Therefore the patient support device 13,15 will only have a soft collision with the examination device 1.

FIG. 5 also shows the first portion 73 of the connector for power and/or signals, which first portion 73 can engage with the second portion 75 of that connector, which second portion 75 is present in the second part 19 of the docking means. After the patient support device 13,15 have reached its final position, said first portion 73 can move forward to contact said second portion 75.

FIG. 7 shows a portion of the first part 21 of the docking means without the plate-like guiding member 57. Underneath the guiding member 57 there are two snap members 77, which can pivot around the vertical pins 79. The two snap members 77 are kept in their outward position, as shown in FIG. 7, by the helical springs 81. The two snap members 77 comprise the said recesses 71, which can cooperate with the two protrusions 69 of the second part 19 of the docking means.

During the docking operation, the two protrusions 69 (FIG. 6) of the second part 19 of the docking means will push the two snap members 77 inwards, i.e. towards each other, up to the moment that the protrusions 69 reach the respective recesses 71. At that moment the snap members 77 will move outwards again, forced by the two helical springs 81, resulting in the mutual fixation of the two parts 19,21 of the docking means. To uncouple the two parts 19,21 of the docking means, a pneumatic cylinder 83 can pull the two snap members 77 towards each other.

Underneath the plate 87, on which the snap members 77 are mounted, there is the first portion 73 of the connector. Said first portion 73 can move forward to engage with the second portion 75 (see FIG. 6) of the connector. The FIGS. 5, 7 and 8 show said first portion 73 in its forward position, whereby two cover elements 89 are displaced away from each other. That forward position is established after the two parts 19,21 of the docking means are connected to each other. Before the two parts 19,21 are uncoupled, said first portion 73 returns in its backward position, whereby the two cover elements 89 are moved towards each other to close the opening 91 (see FIG. 5) through which the first portion 73 of the connector can move forward.

FIG. 8 shows a portion of the first part 21 of the docking means, which portion is located underneath the plate 87 (see FIG. 7). Both cover elements 89 can pivot around vertical pin 93 and spring means (not shown) are pulling the two cover elements 89 together, so that the opening 91 (FIG. 5) is closed. Push member 95, mounted on the moving first portion 73 of the connector, can push the two cover elements 89 outward during the forward movement of said first portion 73, so that said first portion 73 can move forward through opening 91 to engage with second portion 75 of the connector.

The embodiment of the system as described above is merely an example; a great many other embodiments are possible.

What is claimed is:

1. A medical system for examination or treatment of a patient, comprising an examination device, a patient support device, and docking means for connecting both said devices to each other, the docking means comprising a first part provided with a guiding member having a guiding surface and a second part provided with guiding elements for contacting the guiding surface, whereby each of said parts is attached to one of said devices, characterized in that the guiding member comprises two substantially vertical guiding surfaces, positioned symmetrically with respect to a vertical plane through the device to which the first part of the docking means is attached, whereby the distance between said two guiding surfaces decreases further away from the device to which said first part is attached, characterized in that said guiding element comprises a roller.

2. A medical system as claimed in claim 1, characterized in that said first part of the docking means is attached to said examination device.

3. A medical system as claimed in claim 1, characterized in that said guiding member is movable in one horizontal direction towards and away from the device to which said first part is attached.

4. A medical system as claimed in claim 1, characterized by means for pushing the guiding member in a position away from the device to which said first part is attached.

5. A medical system as claimed in claim 1, characterized in that said guiding member is a substantial horizontal plate-like element, whereby the edge of said plate-like element forms said guiding surface.

6. A medical system as claimed in claim 1, characterized in that said docking means are located at the lower parts of said devices.

7. A medical system as claimed in claim 1, characterized by coupling means for fixing said first part to said second part of the docking means after the two parts are moved towards each other.

8. A medical system as claimed in claim 7, characterized in that said coupling means comprise two protrusions of said second part and two corresponding recesses in said first part, the recesses being located at both substantial vertical opposite sides of said first part.

9. A medical system as claimed in claim 8, characterized in that said recesses and portions of said first part near said recesses can move towards each other.

10. A medical system as claimed in claim 1, characterized in that the docking means comprise a connector for power and/or signals, which connector comprises a first portion in said first part and a second portion in said second part of the docking means, whereby said portions are movable towards each other for mutual engagement after both said devices are connected to each other.

11. A medical system for examination or treatment of a patient, comprising an examination device, a patient support device, and docking means for connecting both said devices to each other, the docking means comprising a first part provided with a guiding member having a guiding surface and a second part provided with guiding elements for contacting the a guiding surface, whereby each of said parts is attached to one of said devices, characterized in that the guiding member comprises two substantially vertical guiding surfaces, positioned symmetrically with respect to a vertical plane through the device to which the first part of the docking means is attached, whereby the distance between said two guiding surfaces decreases further away from the device to which said first part is attached, characterized in that said guiding member is movable with respect to the said first part of the docking means.

12. A medical system for examination or treatment of a patient, comprising an examination device, a patient support device, and docking means for connecting both said devices to each other, the docking means comprising a first part provided with a guiding member having a guiding surface and a second part provided with guiding elements for contacting the guiding surface, whereby each of said parts is attached to one of said devices, characterized in that the guiding member comprises two substantially vertical guiding surfaces, positioned symmetrically with respect to a vertical plane through the device to which the first part of the docking means is attached, whereby the distance between said two guiding surfaces decreases further away from the device to which said first part is attached, characterized by damping means for braking down the movement of the guide member when it reaches its final position whereby the two parts of the docking means are interconnected.

13. A medical system as claimed in claim 12, characterized in that said means for damping comprise a pneumatic cylinder counter-acting the movement of the guiding member, especially the last portion of the movement towards the device to which said first part is attached.

* * * * *